(12) United States Patent
Del Soldato et al.

(10) Patent No.: US 7,166,605 B2
(45) Date of Patent: Jan. 23, 2007

(54) PROBUCOL NITRO-DERIVATIVES

(75) Inventors: Piero Del Soldato, Monza (IT); Giancarlo Santus, Milan (IT); Ennio Ongini, Segrate (IT)

(73) Assignee: Nicox, S.A., Sophia Antipolis (FR)

( * ) Notice: Subject to any disclaimer, the term of this patent is extended or adjusted under 35 U.S.C. 154(b) by 0 days.

(21) Appl. No.: 10/503,128

(22) PCT Filed: Mar. 19, 2003

(86) PCT No.: PCT/EP03/02850

§ 371 (c)(1),
(2), (4) Date: May 23, 2005

(87) PCT Pub. No.: WO03/080568

PCT Pub. Date: Oct. 2, 2003

(65) Prior Publication Data

US 2006/0167003 A1     Jul. 27, 2006

(30) Foreign Application Priority Data

Mar. 22, 2002   (IT) .......................... MI2002A0597

(51) Int. Cl.
*A01N 43/58* (2006.01)
*A61N 43/60* (2006.01)

(52) U.S. Cl. ................. 514/252.12; 514/509; 514/706; 544/399; 568/64; 424/43; 424/46; 424/400; 424/424; 424/436; 424/449; 424/450; 424/451; 424/464; 424/489

(58) Field of Classification Search ................ 514/712, 514/252.12, 509, 706; 436/71; 435/7.1; 544/399; 568/64; 424/43, 46, 400, 450, 424/451, 464, 469, 436, 449
See application file for complete search history.

(56) References Cited

U.S. PATENT DOCUMENTS

| 4,985,465 A | 1/1991 | Hendler |
| 5,262,439 A | 11/1993 | Parthasarathy |
| 6,121,319 A | 9/2000 | Somers |

FOREIGN PATENT DOCUMENTS

| FR | 2 140 769 | | 1/1973 |
| FR | 2 140 771 | | 1/1973 |
| FR | 2 168 137 | | 8/1973 |
| WO | WO 9831225 | * | 7/1998 |
| WO | WO 9842327 | * | 10/1998 |
| WO | WO 98/51289 | | 11/1998 |
| WO | WO 9851662 | * | 11/1998 |
| WO | WO 99/24400 A1 | | 5/1999 |
| WO | WO 2000028332 | * | 5/2000 |
| WO | WO 01/77072 A2 | | 4/2001 |
| WO | WO 01/70757 A2 | | 9/2001 |

OTHER PUBLICATIONS

Zimetbaum et al., "Probucol: Pharmacology and Clinical Application", *J. Clin. Pharmacol.* 30, 3-9, 1990.
Kaul et al., "Probucol treatment reverses antioxidant and functional deficit in diabetic cardiomyopathy", *Mol. Cell. Bichem,* 160/161, 283-288, 1996.
Regnström et al., "The effect of probucol on low density lipoprotein oxidation and femoral atherosclerosis", *Atheroscloerosis* 125, 217-229, 1996.
Lee et al., "Effectiveness of Probucol in Preventing Restenosis after Percutaneous Transluminal Coronary Angioplasty", *Jpn. Heart J.* 37(3) 327-332, 2002.
Ishizaki et al., "Effect of probucol, an oral hypocholesterolaemic agent, on acute tobacco smoke inhalation in rats", *Clinical Sci.* 90, 517-523, 1996.
Heel et al., "Probucol: A Review of its Pharmacological Properties and Therapeutic Use in Patients with Hypercholesterolaemia", *Drugs* 15, 409-428, 1978.
Reinoehl et al., "Probucol-associated tachyarrhythmic events and QT prolongatrion: Importance of gender"*Am. Heart J.* 131(6), 1184-1191, 1992.
Steinberg et al., "Beyond Cholesterol: Modifications of Low-Density Lipoprotein That Increase Its Atherogenicity", *New Eng. J. Med.* 320(14), 915-924, 1989.
Heeg et al., "Taux plasmatiques du probucol chez l'homme aprés administration orale unique ou repetee", Nouv. Presse Med. 9(40), 2990-2994, 1980.

* cited by examiner

*Primary Examiner*—Thurman Page
*Assistant Examiner*—Chukwuma Nwaonicha
(74) *Attorney, Agent, or Firm*—Arent Fox PLLC

(57) ABSTRACT

Probucol derivatives and pharmaceutical compositions containing the same to be employed in treatment or prophylaxis of diseases.

28 Claims, No Drawings

PROBUCOL NITRO-DERIVATIVES

CROSS-REFERENCE TO RELATED APPLICATION

This application is a National Stage entry of International Application No. PCT/EP03/02850, filed Mar. 19, 2003, the entire specification claims and drawings of which are incorporated herewith by reference.

The present invention relates to new probucol derivatives, pharmaceutical compositions containing them and their use for the treatment of endothelial diseases, oxidative stress, cardiovascular and inflammatory diseases, cardiovascular diseases, ocular diseases, autoimmune diseases, neurological disorders and cancer as well as for the treatment of hypercholesterolemia and hyperlipidemia.

Probucol is a well known antioxidant, its full chemical name being 4,4'-(isopropylidenedithio)-bis(2,6-di-tert-butylphenol). Probucol has been primarily used to lower serum cholesterol levels in hypercholesterolemic patients (Zimetbaum, J. Clin. Pharmacol. 30:3–9, 1990). However, it has also been used to treat a variety of infections, traumas and pathologic conditions, for example in the treatment of diabetic cardiomyopathy (Kaul, Mol. Cell. Biochem., 160–161: 283–8, 1996), femoral atherosclerosis (Regnstrom, Atherosclerosis 125:217–28, 1996), restenosis (Lee, Jpn. Heart J., 37:327–32, 1996), HIV infections (U.S. Pat. No. 4,985,465) and smoke inhalation damage (Ishizaki, Clin. Sci., 90:517–23, 1996).

Probucol is commonly administered in the form of tablets available under the trademark Lorelco®. Solid probucol is poorly absorbed into the blood, and is excreted in substantially unchanged form. Further, the tablet form of probucol is absorbed at significantly different rates and in different amounts by different patients. In a study carried out in 1980, peak levels of probucol in sera were found to differ by as much as a factor of 20 from patient to patient (Heeg et al., Plasma Levels of Probucol in Man After Single and Repeated Oral Doses, La Nouvelle Presse Medicale, 9:2990–2994, 1980).

In view of the foregoing, an alternative probucol delivery formulation would be highly desirable, which has improved absorption characteristics and stability properties.

U.S. Pat. No. 5,262,439 discloses analogs of probucol, in which one or both of the hydroxyl groups are replaced with ester groups. The described derivatives are selected from the group consisting of mono- or di-succinic acid ester, glutaric acid ester, adipic acid ester, suberic acid ester, sebacic acid ester, azelaic acid ester and maleic acid ester or the probucol derivative is a mono- o di-ester in which the ester contains an alkyl or alkenyl group that contains a functionality selected from the group consisting of carboxylic acid group, amine group, salt of an amine group, amide group and aldehyde group.

A series of French patents disclose that certain probucol derivatives are hypocholesterolemic and hypolipemic agents, wherein bis 4-hydroxyphenylthioalkane esters (FR-A-2,168,137), tetralinyl phenoxy alkanoic esters of probucol (FR-A-2,140,771) and benzofuryloxyalkanoic acid derivatives of probucol (FR-A-2,140,769) are expressly mentioned.

U.S. Pat. No. 6,121,319 describes a method for the treatment of cardiovascular and inflammatory diseases, comprising administering a monoester of probucol, wherein the monoester includes a functional moiety selected from the group consisting of saturated and unsaturated dicarboxylic acids and salts thereof, amino carboxylic acids and salts thereof, and aldehyde containing carboxylic acids and salts thereof.

WO 01/70757 discloses probucol derivatives for the treatment of inflammatory disorders, cardiovascular diseases, ocular diseases, autoimmune diseases, neurological disorders and cancer, in which a hydroxylic group of probucol is substituted for example by a substituted or unsubstituted carbohydrate, alditol, alkyl or substituted alkyl terminated by phosphonic o sulfonic acid.

WO 99/24400 discloses probucol derivatives, in which one or both the phenyl hydroxyl groups of the molecule are replaced with ester groups. The new derivatives are effective for the treatment of artherosclerosis and viral infections and are proposed as antioxidant for inhibiting oxidative damage for example in patients to which thrombolytic agents have been administered for example to prevent a myocardial infarction.

In U.S. Pat. No. 4,985,465 a method for inhibiting viral and retroviral infections is disclosed, comprising administering to living organisms an effective amount of a probucol derivative having different alkyl substituents on both the phenyl rings, but in which both the phenyl hydroxyl groups are not esterified.

Now, it has been reported that probucol has side-effects both at gastrointestinal level, such as for example diarrhoea, nausea, abdominal pain, and also on cardiovascular system (Drugs 15: 409–428, 1978). Further studies have also ascertained idiosyncratic reaction characterized by dizziness and palpitations and the occurrence of ventricular tachyarrhythmias in patients to which probucol has been administered. It has been also reported that a probucol therapy could cause a QT prolongation, and therefore it should not be administered to patients with ventricular instability in which QT interval is altered (Reinoehl et al., American Heart Journal, vol. 131, no. 6, 1184–1190).

It is known that VCAM-1, vascular cell adhesion molecule-1, is important in mediating the selective adhesion of mononuclear leukocytes. Subsequent conversion of leukocytes to foamy macrophages results in the synthesis of a wide variety of inflammatory cytokines, growth factors, and chemoattractans that help propagate the leukocyte and platelet recruitment, smooth muscle cell proliferation, endothelial cell activation, and extracellular matrix synthesis characteristic of maturing atherosclerotic plaque. Given the growing body of evidence implicating inflammation and VCAM-1 expression in cardiovascular disease and other disease states such as rheumatoid arthritis and multiple sclerosis, there is a need to identify new active ingredients for reducing inflammation and VCAM-1 expression.

It is also known that hypercholesterolemia is an important risk factor associated with cardiovascular disease. Serum lipoproteins are the carriers for lipids in the circulation. Chylomicrons primarily participate in transporting dietary triglycerides and cholesterol from the intestine to adipose tissue and liver. VLDL (very low-density lipoproteins) deliver endogenously synthetized triglycerides from liver to adipose tissue and other tissues. LDL (low-density lipoproteins) transports cholesterol to pheripheral tissues and regulate endogenous cholesterol levels in those tissues, whereas HDL (high-density lipoproteins) transports cholesterol from peripheral tissues to liver. Steinberg et al. (N. Eng. J. Med., 1989, 320:915–924) hypothesized that modification of LDL in oxidatively modified LDL (ox-LDL) is the central event that initiates and propagates atherosclerosis. Through a mechanism that is not well defined, areas of vessel wall predisposed to atherosclerosis preferentially sequester circulating LDL. Endothelial, smooth muscle, and/or inflammatory cells then convert LDL to ox-LDL. Cholesterol is carried in the blood of warm-blooded animals in certain lipid-protein complexes such as chylomicrons, VLDL, LDL e HDL. It is widely accepted that LDL functions in a way that directly results in deposition of the LDL cholesterol in the blood vessel wall and that HDL functions in a way that results in the HDL picking up cholesterol from the vessel wall and transporting it to the liver where it is metabolized. LDL cholesterol levels correlate well with the risk of coronary heart disease whereas the HDL cholesterol levels are inversely associated with coronary heart disease. In patients with low levels of LDL, the development of atherosclerosis is rare.

It is believed that peroxidation of LDL lipid is an important perequisite to the facilitated accumulation of cholesterol in the vessel wall and the subsequent formation of an atherosclerotic plaque. Being a strong antioxidant, probucol is thus able to block oxidative modification of LDL.

In one of the literature sources mentioned above (U.S. Pat. No. 6,121,319), it was expressly stated that probucol monoesters block the induced expression of the endothelial cell surface adhesion molecule VCAM-1, they are useful in the treatment of any disease that is mediated by VCAM-1, including cardiovascular and inflammatory diseases as well as hypercholesterolemia and hyperlipidemia, whereas diesters do not significantly affect VCAM-1 expression.

It was an object of the present invention to provide new probucol derivatives having better effectiveness and tolerability, that are free from the above mentioned side effects and thus could be employed for the treatment of endothelial diseases, oxidative stress, inflammatory disorders, cardiovascular diseases, ocular diseases, neurological disorders, cancer, hyperlipidemia and hypercholesterolemia.

Object of the present invention are therefore probucol nitro-derivatives and/or pharmaceutically acceptable salts thereof and pharmaceutical compositions containing them as well as their use for treating endothelial disorders, oxidative stress, VCAM-1 mediated diseases including inflammatory disorders, cardiovascular diseases, ocular diseases, autoimmune diseases, neurological disorders, cancer and to treat hypercholesterolemia and hyperlipidemia. The new nitro-derivatives of the invention can be particularly employed to treat the following diseases selected from the group comprising, but not limited to, rheumatoid arthritis, osteoarthritis, inflammatory bowel disease, Crohn's disease, asthma, allergic rhinitis, sinusitis, chronic obstructive pulmonary disease, dermatitis, psoriasis, cystic fibrosis, multiple sclerosis, vasculitis, organ transplantation rejection, atherosclerosis, post-angioplasty restenosis, coronary artery disease, angina, small artery disease, diabetes mellitus, diabetic nephropathy and diabetic retinopathy, uveitis, macular degeneration, systemic lupus erythematosus, autoimmune type-1 diabetes, Alzheimer's and Parkinson's disease, tumor metastasis and angiogenesis.

In one first aspect, the present invention provides therefore probucol derivatives and/or pharmaceutically salts thereof of general formula (I)

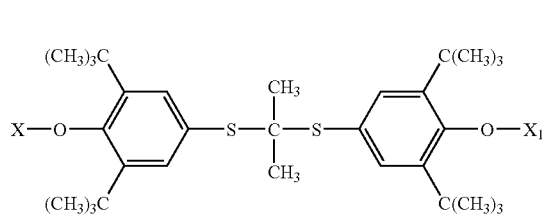

(I)

wherein X e $X_1$ are the same or different and are selected from a hydrogen atom, a group of formula (II)

$(T)_n$—Y—$NO_2$     (II)

with the proviso that X e $X_1$ can not be both hydrogen, wherein n is an integer of from 0 to 1, where when n=1, T means (CO), Y is a bivalent radical having the following meanings:

a) $R^1O$, wherein $R^1$ is:

straight or branched $C_1$–$C_{20}$-alkylene, eventually containing one or more heteroatoms selected from the group consisting of oxygen, nitrogen, sulfur, or one or more groups selected from —O(CO)—, NH(CO)—, —S(CO)—, eventually substituted with one or more of the following groups —OH, —SH, —$NH_2$, —NH-$COR^2$, where $R^2$ is straight or branched $C_1$–$C_{10}$-alkyl, preferably $CH_3$;

cycloalkylene with from 5 to 7 carbon atoms within the cycloalkylene ring, where one or more carbon atoms can be replaced by heteroatoms selected from the group consisting of nitrogen, oxygen and sulfur, and the ring may be substituted with side chains $R^2$, $R^2$ being as defined above;

b)

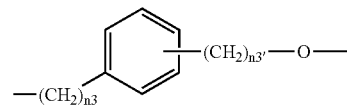

c)

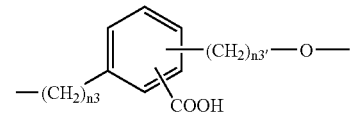

wherein n3 is an integer of from 0 to 20, and n3' is an integer of from 1 to 20, d)

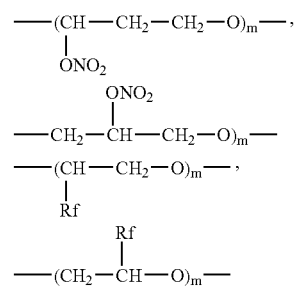

where m is an integer of from 1 to 6, preferably from 1 to 4, Rf is hydrogen or $CH_3$ e)

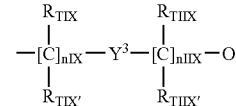

where:

nIX is an integer of from 0 to 10;

nIIX is an integer of from 1 to 10;

$R_{TIX}$, $R_{TIX'}$, $R_{TIX''}$, $R_{TIX'''}$ are the same or different and are H or straight or branched $C_1$–$C_4$-alkyl, preferably $R_{TIX}$, $R_{TIX'}$, $R_{TIX''}$, $R_{TIX'''}$ are H;

$Y^3$ is a 5 or 6-membered heterocyclic saturated, unsaturated or aromatic ring containing one or more heteroatoms selected from the group consisting of nitrogen, oxygen and sulfur, and it can be selected from the group consisting of

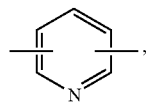
(Y1)

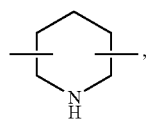
(Y2)

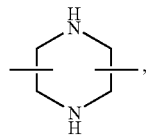
(Y3)

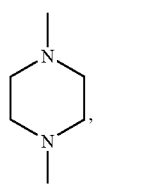
(Y4)

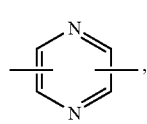
(Y5)

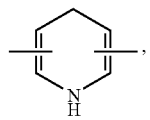
(Y6)

(Y7)

-continued

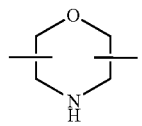
(Y8)

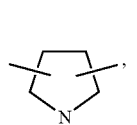
(Y9)

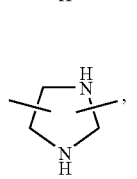
(Y10)

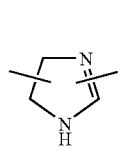
(Y11)

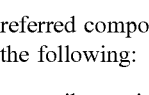
(Y12)

Preferred compounds according to the present invention are the following:

4-nitrooxyibutanoic acid, [4-[[1-[[3,5-bis(1,1-dimethylethyl) -4-hydroxy-phenyl]thio]-1-methylethyl]-thio]-2,6-bis(1,1-dimethylethyl)phenl]ester;

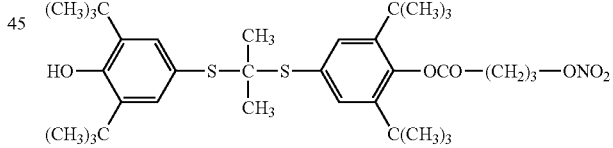

4-nitrooxybutanoic acid, (1-methylethylidene) bis-[thio[2,6-bis(1,1-dimethylethyl)-4,1-phenylene]]ester

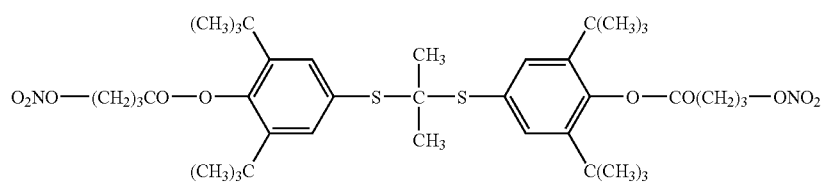

phenol, [4-[[1-[[3,5-bis(1,1-dimethylethyl)-4-[4-(nitrooxy) butoxy]phenyl]-thio]-1-methylethyl]thio]-2,6-bis(1,1-dimethylethyl)

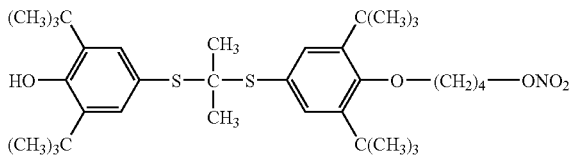

acetone, bis[3,5-(1,1-dimethylethyl)-4-(4-nitrooxybutoxy) phenyl]-mercaptol

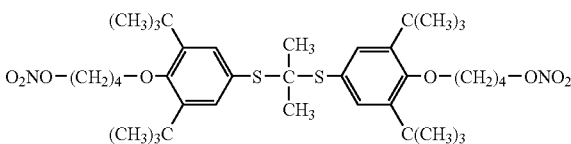

4-(nitrooxymethyl)benzoic acid [4-[[1-[[3,5-bis (1,1-dimethylethyl)-4-hydrohyphenyl]thio]-1-methylethyl]thio]-2,6-bis(1,1-dimethylethyl)phenyl]-ester

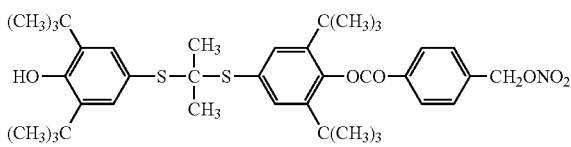

2-[4-(3-nitrooxypropyl)-1-piperazinyl]acetic acid, [4-[[1-[[3,5-bis(1,1-dimethylethyl)-4-hydroxyphenyl]thio]-1-methylethyl]thio]-2,6-bis (1,1-dimethylethyl) phenyl]-ester

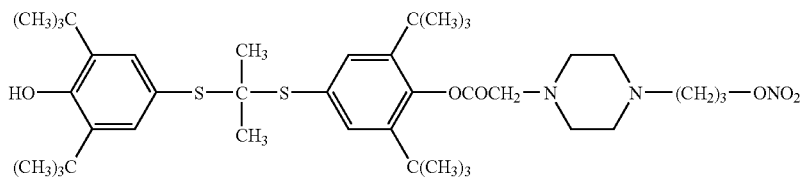

In a further aspect, the present invention provides pharmaceutical compositions which comprise a compound of the general formula reported above in combination with a pharmaceutical acceptable carrier. The daily dose of active ingredient administered to a host can be a single dose or it can be an effective amount divided into several smaller doses that are to be administered throughout the day. Usually, total daily dose may be in amounts from 1 to 2000 mg, preferably from 10 to 1000 mg, in particular from 50 to 500 mg. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation spray o aerosol, in dosage unit formulations containing conventional non-toxic pharmaceutically acceptable carriers, adjuvants and vehicles as desired. Topical administration may also involve the use of transdermal administration such as transdermal patches or iontophoresis devices. The term "parenteral" as used herein includes subcutaneous injections, intravenous, intramuscular, intrasternal injection or infusion techniques.

Injectable preparations, for example, sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent o solvent. Among the acceptable vehicles and solvents are water, Ringer's solution and isotonic sodium chloride solution. In addition, sterile, fixed oils are conventionally employed as a solvent or suspending medium. For this purpose any bland fixed oil may be employed including synthetic mono- or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and the like.

Experimentals: Synthesis Procedure

When the compounds utilized in the synthesis described below contain several functional groups that could interfere during the reaction, said groups can be protected in advance according to methods known in the art, for example as described n T. W. Greene "Protective groups in organic synthesis", Harward University Press, 1980. Generally, the suitable acylic chlorides are products available on the market or they can be prepared from the corresponding acids by procedures known from literature.

When n=1 and T=(CO), the probucol derivatives of formula (I) can be synthetized according to reactions known to those skilled in the art.

I) A method for obtaining probucol esters include for example a first step in which the probucol salt was prepared reacting probucol in a suitable organic solvent, for example tetrahydrofuran, dimethylformamide etc., with a strong base such as NaH, NaOH, KOtBu, generally under inert gas atmosphere, e.g. nitrogen or argon.

The probucol salt thus obtained was then reacted with an acyl halide of formula M-Y'-COCl, where M is halogen such as chlorine, bromine, iodine, OH or $ONO_2$ and Y' has one of the meanings mentioned above for Y under a)–e), however without the terminal oxygen atom.

At the end of the reaction, the desired probucol mono or diester was isolated from the mixture by means of conventional purification procedures, for example chromatography on silica gel, crystallization etc.

When M is different from $ONO_2$, the corresponding nitrooxyderivative was then obtained from the compound isolated as described above, employing for example one of the following procedures:

Ia) when M=halogen, the derivative isolated in the previous reaction step was reacted with $AgNO_3$ in a suitable organic solvent, such as acetonitrile, tetrahydrofuran etc., at a temperature of from 25° C. to 80° C. At the end of the reaction, the silver salt thus formed was separated by filtration and the raw substance was purified with conventional purification procedure, for example chromatography on silica gel, crystallization etc.

Ib) When M=OH, the isolated derivative was subjected to halogenation with for example $PBr_3$, $PCl_5$, $SOCl_2$, $I_2$+triphenylphosphine, and then it was reacted with $AgNO_3$ in a suitable organic solvent, such as acetonitrile, tetrahydrofuran etc. at a temperature of from 25° C. to 80° C. At the end of the reaction, the silver salt thus formed was separated by filtration and the crude material was purified by usual purification techniques, for example by chromatography on silica gel, crystallization etc.

When n=0, the probucol derivatives of formula (I) can be prepared utilizing phenol alkylation reactions well known from literature.

II) A standard procedure is for example the Mitsunobu reaction, according to which probucol, dissolved in a suitable aprotic solvent, such as tetrahydrofuran, was reacted for example with triphenylphosphine, diethyl azodicarboxylate (DEAD) and with a compound of formula HO—Y-M, wherein M and Y are as defined above, under inert nitrogen atmosphere, at the solvent boiling temperature and for a period of from 2 to 10 hours. At the end of the reaction, from the crude mixture the desired ether was isolated for example by chromatography on silica gel.

The nitrooxyderivate was obtained from the compound isolated in the step described above, employing for example one of the procedures mentioned in Ia or in Ib.

III) A further method for obtaining probucol ethers includes the preparation of the salt by reacting probucol in a suitable organic solvent, such as tetrahydrofuran, dimethylformamide etc., with a strong base, such as NaH, NaOH, KOtBu, and treating the salt thus formed with a compound of formula Z-Y-M, where Z is selected from the group consisting of halogen, chlorine, bromine, iodine, or an alcohol derivative, for example mesylate, tosylate, triflate, and M and Y are as defined above. The reaction mixture comprising probucol monoethers and diethers was separated by chromatography on silica gel and, when M is different from $ONO_2$, the desired derivative was transformed into the corresponding nitrooxyderivative employing one of the procedures mentioned in Ia or in Ib The compounds of formula M-Y'—COCl, wherein M is halogen or OH, can be obtained from the corresponding acids of formula M-Y'—COOH by procedures known to a person skilled in the art. When M is $ONO_2$, the compound can be prepared transforming first the acid of formula halo-Y—COOH in the corresponding nitro derivative by reaction with silver nitrate in order to exchange the halo group with a nitro moiety, then the acid chloride was synthesized according to reactions well known in literature.

The following example are offered to further illustrate, but not to limit, the claimed invention.

REFERENCE EXAMPLE

Synthesis of 4-nitrooxybutanoic acid

4-Bromobutanoic acid (1.00 g, 6.0 mmol) was dissolved in acetonitrile (15 ml) and the resulting mixture was poured in a three neck flask, kept under argon and in absence of light. Magnetic stirring was set on. The solution was then cooled to 5° C. with an ice bath and silver nitrate (1.22 g, 7.2 mmol) was slowly added. The mixture was allowed to react for 4 hours at 5° C. The TLC control (EtOAc/petroleum ether 3:7 as eluent) evidenced the residual presence of unreacted starting material. Further silver nitrate was added (310 mg, 1.8 mmol) and stirring was continued overnight at room temperature. The solution was filtered to remove silver salts, poured in 100 ml of brine and extracted with $CH_2Cl_2$ (2×50 ml). The organic phase was dried on $MgSO_4$ and concentrated at reduced pressure to give 850 mg of the crude title compound, which was checked by IR and 1H NMR spectroscopy. The obtained nitroderivative was employed in the next step without further purification.

IR (oil) $cm^{-1}$: 3521 (OH), 1770 (C=O), 1627, 1282 (—$ONO_2$). 1H NMR (CDCl3): δ 2.27 (m, 2H, —$CH_2$—), δ 2.54 (t, 2H, —$CH_2$—COOH), δ 2.27 (t, 2H, —$CH_2$—$ONO_2$), δ 11.9 (s, 1H, —COOH).

Synthesis of 4-nitrooxybutanoyl chloride

In a three neck flask kept under argon and containing 90 ml of $CH_2Cl_2$, 4-nitrooxybutanoic acid (800 mg, 5.3 mmol) prepared as described above was charged. Then $PCl_5$ was added in one portion (1.25 g, 6.0 mmol) and the resulting mixture was stirred at room temperature. The reaction was checked by IR spectroscopy. After ca. 2 hours stirrer was removed and the reaction mixture was distilled under vacuum. The crude chloride (900 mg, 5.4 mmol) was used in the further steps without purification.

Further acid chlorides can be obtained in a similar manner, starting from several, different nitrooxy-acids, in which the butanoyl moiety was replaced by other appropriate radicals that can be straight or branched aliphatic, aromatic, heterocyclic or heteroaromatic according to the desired end products.

Example 1

Synthesis of 4-nitrooxybutanoic acid, (1-methylethylidene)bis[thio[2,6-bis(1,1-dimethylethyl)-4,1-phenylene]] ester

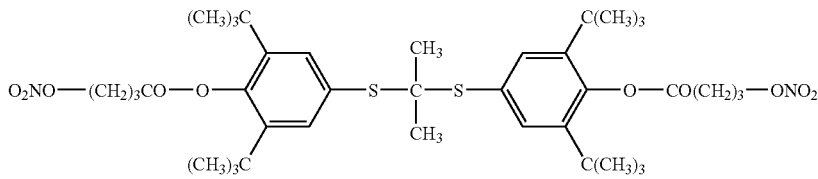

A) Synthesis of 4-bromobutanoic acid, (1-methylethylidene)bis[thio[2,6-bis(1,1-dimethylethyl)-4,1-phenylene]]ester To a solution of KOtBu (5 g, 45 mmol) in anhydrous THF (100 ml), in small portions, under stirring and at room temperature probucol was added (11 g, 21 mmol), maintaining then the temperature between 40° C. and 25° C. When adding is over, the mixture was further stirred for 1 hour, then 4-bromobutyryl chloride (13,72 g, 74 mmol) was added. After 2 hours, the solvent was evaporated from the mixture at reduced pressure, the residue was dissolved in ethyl acetate, the organic phases were washed with water and then dried over anhydrous sodium sulphate and the solvent was removed at reduced pressure. The crude substance was purified by chromatography on silica gel with a mixture of ethyl acetate/hexane (4/6 v/v) as eluent, to give 4-bromobutanoic acid (1-methylethylidene)bis[thio[2,6-bis (1,1-dimethylethyl)-4,1-phenylene]]ester (1.5 g). B) Synthesis of 4-nitrooxybutanoic acid (1-methylethylidene)bis[thio[2,6-bis (1,1-dimethylethyl)-4,1-phenylene]]ester To a solution of 4-bromobutanoic acid (1-methylethylidene)bis[thio[2,6-bis (1,1-dimethylethyl)-4,1-phenylene]]ester (1.4 g, 1.72 mmol) in acetonitrile/THF (75 ml, 2/1 v/v) AgNO$_3$ was added (0.8 g, 4.7 mmol) and the solution was heated at 60° C. in the dark for 6 hours. The silver salt (AgBr) was then filtered off and the solvent was evaporated at reduced pressure. The crude substance was purified by chromatography on silica gel employing a mixture of ethyl acetate/hexane (4/6 v/v) as eluent to give 4-nitrooxybutanoic acid (1-methylethylidene)bis[thio[2,6-bis(1,1-dimethylethyl)-4,1-phenylene]]ester (500 mg).

$^1$H NMR (CDCl$_3$) ppm: 7.02 (4H, s); 4.45 (4H, t); 3.67 (4H, t); 2.64–2.56 (4H, m); 1.45 (36H, s); 1.28 (6H, s).

Example 2

4-Nitrooxybutanoic acid [4-[[1-[[3,5-bis (1,1-dimethylethyl)-4-hydroxyphenyl]thio]-1-methylethyl]thio]-2,6-bis (1,1-dimethylethyl)phenyl]ester

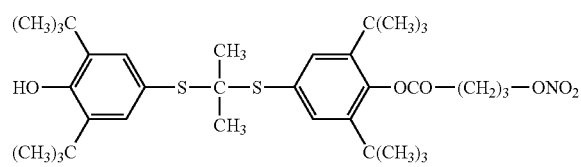

A) Synthesis of 4-bromobutanoic acid [4-[[1-[[3,5-bis(1,1-dimethylethyl)-4-hydroxyphenhyl]thio]-1-methylethyl]thio]-2,6-bis(1,1-dimethylethyl)-phenyl]ester To a solution of probucol (800 mg, 1.54 mmol) in anhydrous THF (25 ml), NaH was added (2.31 mmol, 92 mg of a 60% dispersion of NaH in mineral oil) under stirring and at room temperature. The mixture was stirred for further 30 minutes, then 4-bromobutyryl chloride was added (560 mg, 3.2 mmol). The mixture was stirred for 50 hours, then diluted with Et$_2$O (250 ml), the organic phases were washed with water and then dried over anhydrous sodium sulphate and the solvent was evaporated off at reduced pressure. The product thus obtained was purified by chromatography on silica gel with a mixture of hexane/ethyl acetate (7/3 v/v) as eluent to give 4-bromobutanoic acid, [4-[[1-[[3,5-bis(1,1-dimethylethyl)-4-hydroxyphenyl]thio]-1-methylethyl]thio]-2,6-bis(1,1-dimethylethyl)phenyl]ester (200 mg).

B) 4-Nitrooxybutanoic acid, [4-[[1-[[3,5-bis (1,1-dimethylethyl)-4-hydroxyphenyl]thio]-1-methylethyl)]thio]-2,6-bis (1,1-dimethylethyl)phenyl]ester To a solution of 4-bromobutanoic acid [4-[[1-[[3, 5-bis (1,1-dimethylethyl)-4-hydroxyphenyl]thio]-1-methylethyl]thio]-2,6-bis(1,1-dimethylethyl)phenyl]ester (150 mg, 0.22 mmol) in acetonitrile/THF (15 ml 2/1 v/v), AgNO$_3$ was added (80 mg, 0.47 mmol) and the solution was heated in the dark at 60° C. for 6 hours. The silver salt was then filtered off (AgBr) and the solvent was evaporated at reduced pressure. The product thus obtained was purified by chromatography on silica gel with a mixture of ethyl acetate/hexane as eluent (4/6 v/v) to give 4-nitrooxybutanoic acid, [4-[[1-[[3,5-bis(1,1-dimethyletihyl)-4-hydroxyphenyl]thio]-1-methylethyl]thio]-2,6-bis (1,1-dimethylethyl)-phenyl]ester (100 mg).

$^1$H NMR (CDCl$_3$) ppm: 9.42 (1H, s); 7.02 (2H, s); 6.82 (2H, s); 4.45 (4H, t); 3.67 (2H, t); 2.64-2.56 (2H, m); 1.45 (36H, s); 1.28 (6H, s).

Example 3

The probucol monoester of Example 2 can be alternatively prepared as follows. Probucol (1.00 g, 1.95 mmol) was dissolved in 15 ml of anhydrous THF and the solution was poured in a three neck flask kept under argon. Sodium hydride (150 mg of 60% NaH, 3.9 mmol) was then added under stirring and the mixture was allowed to react for 1 hour at room temperature. To this solution, the crude 4-nitrooxybutanoyl chloride, prepared as described in reference example and dissolved in 5 ml of anhydrous THF, was then added dropwise with a funnel. The resulting mixture was stirred 18 hours at room temperature, checking the reaction by TLC (EtOAc/petroleum ether 3:7 as eluent). Water was added (15 ml) and the organic phase was separated, dried on Na$_2$SO$_4$ and concentrated at reduced pressure. The reaction product was analysed by LC/MS ESI employing a RP-C18 4.6×100 ml column. M/Z 646.3, corresponding to the monoesterification product, was detected as a shoulder of the main reaction product peak.

Replacing the nitrooxybutanoyl chloride with several, different nitrooxy derivatives, in a similar way further mono or diesters can be obtained.

The invention claimed is:

1. A compound of general formula (I) and/or salts thereof

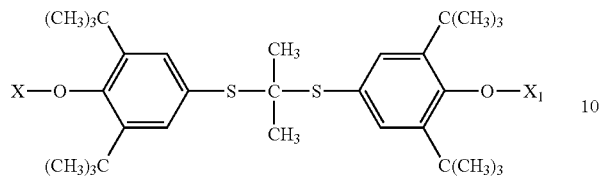

wherein X and $X_1$ are the same or different and are selected from hydrogen and a group of formula (II)

$(T)_n$—Y—$NO_2$ (II)

with the proviso that X and $X_1$ cannot be both hydrogen, wherein n is an integer of from 0 to 1, where when n=1, T is the group (CO), Y is a bivalent radical having the following meanings:

a) $R^1O$, wherein $R^1$ is:
straight or branched $C_1$–$C_{20}$-alkylene optionally containing one or more heteroatoms selected from the group consisting of oxygen, nitrogen and sulfur, or one or more groups —O(CO)—, —NH(CO)—, —S(CO)—, optionally substituted with one or more of the following: —OH, —SH, —$NH_2$, —$NHCOR^2$, where $R^2$ is straight or branched $C_1$–$C_{10}$-alkyl;
cycloalkylene with from 5 to 7 carbon atoms in the ring, where one or more carbon atoms can be replaced by heteroatoms selected from the group consisting of nitrogen, oxygen and sulfur, and the ring can be substituted with side chains $R^2$, $R^2$ being defined as above;

b) 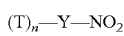

c) 

wherein n3 is an integer of from 0 to 20, and n3' is an integer of from 1 to 20, d) 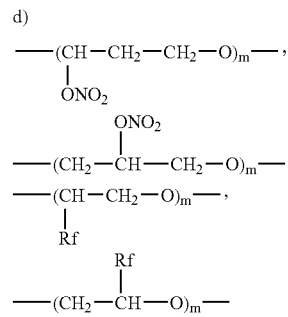

wherein m is an integer of from 1 to 6, Rf is hydrogen or $CH_3$ e) 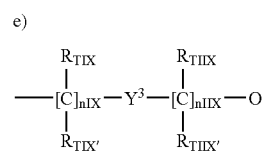

wherein:
nIX is an integer of from 0 to 10;
nIIX is an integer of from 1 to 10;
$R_{TIX}$, $R_{TIX'}$, $R_{TIIX}$, $R_{TIIX'}$ are the same or different and are H or straight or branched $C_1$–$C_4$alkyl;
$Y^3$ is a 5 or 6-membered heterocyclic saturated, unsaturated or aromatic ring containing one or more heteroatoms selected from the group consisting of nitrogen, oxygen and sulfur.

2. A compound of general formula (I) according to claim 1, that is: 4-nitrooxybutanoic , [4-[[1-[[3,5-bis(1,1 dimethylethyl)-4-hydroxyphenyl]thio]-1-methylethyl]thio]-2,6-bis (1,1-dimethylethyl)phenyl]ester

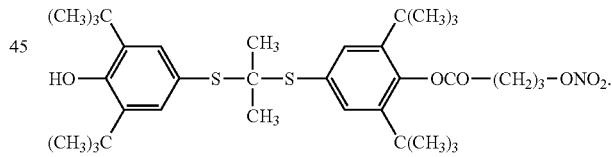

3. A compound of general formula (I) according to claim 1, that is: 4-nitrooxybutanoic acid, (1-methylethylidene)bis [thio[2,6-bis(1,1 dimethylethyl)-4,1-phenylene]]ester

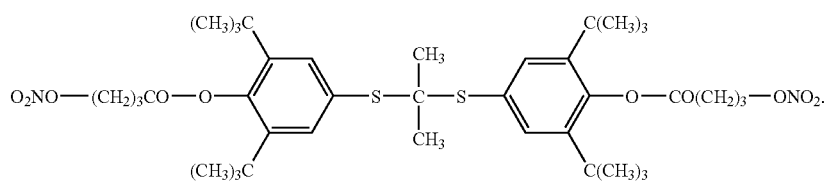

4. A compound of general formula (I) according to claim 1, that is: phenol, [4-[[1-[[3,5-bis(1,1dimethylethyl)-4-[4-(nitrooxy)butoxy]phenyl]-thio]-1-methylethyl]thio]-2,6-bis(1,1-dimethylethyl)

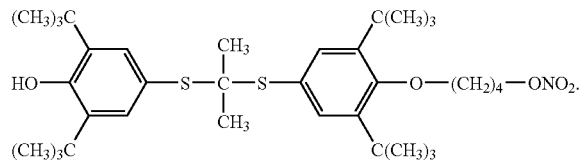

5. A compound of general formula (I) according to claim 1, that is: acetone, bis[3,5-(1,1-dimethylethyl)-4-(4-nitrooxybutoxy)phenyl]-mercaptol

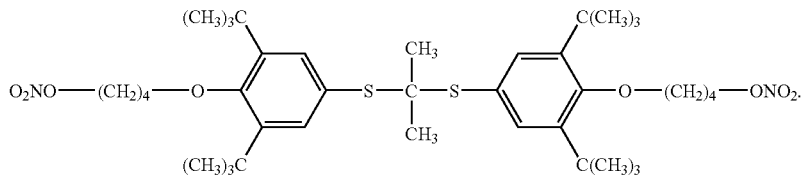

6. A compound of general formula (I) according to claim 1, that is: 4-(nitrooxymethyl) benzoic acid, [4-[[1-[[3,5-bis(1,1-dimethylethyl)-4 hydroxyphenyl]thio]-1-methylethyl]thio]-2,6-bis(1,1 dimethylethyl)phenyl]ester

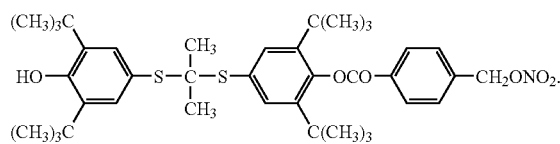

7. A compound of general formula (I) according to claim 1, that is: 2-[4-(3-nitrooxypropyl)-1 piperazinyl]acetic acid, [4-[[1-[[3,5-bis(1,1 dimethylethyl)-4-hydroxyphenyl]thio]-1-methylethyl]thio]2,6-bis(1,1-dimethylethyl)phenyl]ester

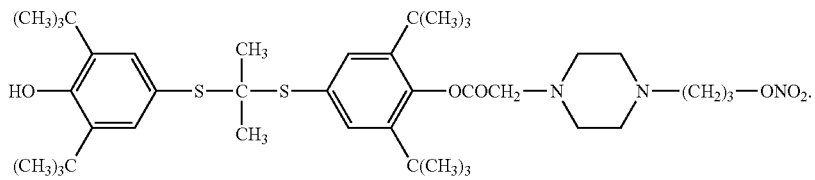

8. A method for treatment of hyperlipidemia and/or hypercholesterolemia comprising administering an effective amount of a compound of general formula I and/or a salt thereof according to claim 1 to a subject.

9. A method for treatment of inflammatory disorders comprising administering an effective amount of a compound of general formula I and/or a salt thereof according to claim 1 to a subject.

10. The method of claim 9, wherein the inflammatory disorders are selected from the group consisting of rheumatoid arthritis, osteoarthritis, asthma, inflammatory bowel disease, Crohn's disease, allergic rhinitis, sinusitis, chronic obstructive pulmonary disease, dermatitis, psoriasis, cystic fibrosis, multiple sclerosis, vasculitis, and organ transplant rejection.

11. A method for treatment of cardiovascular disease comprising administering an effective amount of a compound of general formula I and/or a salt thereof according to claim 1 to a subject.

12. The method of claim 11, wherein the cardiovascular diseases are selected from the group consisting of atherosclerosis, restenosis, coronary artery disease, angina, small artery disease, diabetes mellitus, diabetic nephropathy, diabetic retinopathy, stroke and myocardic infarct.

13. A method for treatment of ocular diseases comprising administering an effective amount of a compound of general formula I and/or a salt thereof according to claim 1 to a subject.

14. The method of claim 13, wherein the ocular diseases are selected from the group consisting of uveitis and macular degeneration.

15. A method of treatment of autoimmune diseases comprising administering an effective amount of a compound of general formula I and/or a salt thereof according to claim 1 to a subject.

16. The method of claim 15, wherein the autoimmune diseases are selected from the group consisting of systemic lupus erythematosus, autoimmune type-1 diabetes and graft versus host disease.

17. A method of treatment of neurological disorders comprising administering an effective amount of a compound of general formula I and/or a salt thereof according to claim 1 to a subject.

18. The method of claim 17, wherein the neurological disorders are selected from the group consisting of Alzheimer's disease, Parkinson's disease and amyotrophic lateral sclerosis.

19. A method of treatment of tumor metastasis and angiogenesis comprising administering an effective amount of a compound of general formula I and/or a salt thereof according to claim 1 to a subject.

20. A method of treatment of VCAM-1 mediated diseases comprising administering an effective amount of a compound of general formula I and/or a salt thereof according to claim 1 to a subject.

21. A method of treatment of endothelial dysfunctions and oxidative stress comprising administering an effective amount of a compound of general formula I and/or a salt thereof according to claim 1 to a subject.

22. A pharmaceutical composition comprising a pharmaceutically acceptable carrier and a pharmaceutically effective amount of a compound of general formula I and/or a salt thereof according to claim 1.

23. A composition according to claim 22 in a suitable form for the oral, parenteral, rectal, topical and transdermic administration, by inhalation spray or aerosol or iontophoresis devices.

24. Liquid or solid pharmaceutical composition for the oral, parenteral, rectal, topical or transdermic administration or inhalation spray or aerosol or iontophoresis devices in the form of tablets, capsules or pills optionally with enteric coating, powders, granules, gels, emulsions, solutions, suspensions, syrups, elixir, injectable forms, suppositories, in transdermal patches or liposomes, containing a compound of formula I according to claim 1 and/or a salt thereof and a pharmaceutically acceptable carrier.

25. The compound of claim 1, wherein $R^2$ is $CH_3$.

26. The compound of claim 1, wherein m is an integer from 1 to 4.

27. The compound of claim 1, wherein $R_{TIX}$, $R_{TIX'}$, and $R_{TIX''}$ are H.

28. The compound of claim 1, wherein $Y^3$ is selected from the group consisting of:

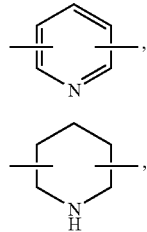
(Y1)

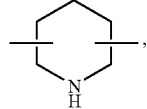
(Y2)

-continued

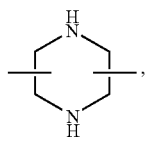
(Y3)

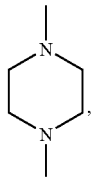
(Y4)

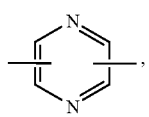
(Y5)

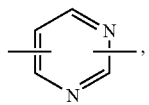
(Y6)

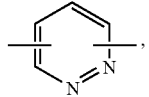
(Y7)

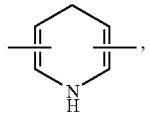
(Y8)

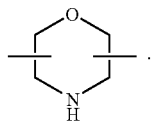
(Y9)

* * * * *